(12) United States Patent
Board et al.

(10) Patent No.: US 11,931,268 B2
(45) Date of Patent: Mar. 19, 2024

(54) TRIAL NECK AND METHOD

(71) Applicant: DEPUY IRELAND UNLIMITED COMPANY, County Cork (IE)

(72) Inventors: Timothy Board, Lancashire (GB); John Bohannon Mason, Charlotte, NC (US); Michael Reeve, Tadcaster (GB); Neil Woollen, Bradford (GB)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 500 days.

(21) Appl. No.: 17/248,665

(22) Filed: Feb. 2, 2021

(65) Prior Publication Data

US 2022/0241092 A1 Aug. 4, 2022

(51) Int. Cl.
A61F 2/46 (2006.01)
A61F 2/36 (2006.01)
A61F 2/30 (2006.01)

(52) U.S. Cl.
CPC .......... *A61F 2/4607* (2013.01); *A61F 2/3609* (2013.01); *A61F 2/4684* (2013.01); *A61F 2002/30476* (2013.01); *A61F 2002/3621* (2013.01); *A61F 2002/3647* (2013.01); *A61F 2002/4629* (2013.01)

(58) Field of Classification Search
CPC ...... A61F 2002/3621; A61F 2002/3647; A61F 2/367; A61F 2/4607; A61F 2002/30616; A61F 2/4684
See application file for complete search history.

(56) References Cited

U.S. PATENT DOCUMENTS

| 5,100,407 | A | 3/1992 | Conrad |
| 5,336,268 | A | 8/1994 | Rispeter |
| 5,569,263 | A | 10/1996 | Hein |
| 5,645,607 | A | 7/1997 | Hickey |
| 5,658,352 | A | 8/1997 | Draenert |
| 5,746,771 | A | 5/1998 | Clement, Jr. |
| 5,766,261 | A | 6/1998 | Neal |
| 6,090,146 | A | 7/2000 | Rozow, III et al. |
| 6,117,138 | A | 9/2000 | Burrows |
| 6,193,759 | B1 | 2/2001 | Ro |
| 6,977,000 | B2 | 12/2005 | Vanasse |

(Continued)

FOREIGN PATENT DOCUMENTS

| DE | 202007009646 U1 | 10/2007 |
| DE | 102007032014 B3 | 10/2008 |

(Continued)

*Primary Examiner* — Alvin J Stewart

(57) ABSTRACT

A trial neck for hip surgery and a method of attaching a trial neck to a femoral canal preparation instrument. The trial neck includes a body portion including a bore for receiving a proximal end of a femoral canal preparation instrument. The trial neck also includes an elongate neck extending from the body portion. The trial neck further includes a locking mechanism comprising a lever. The lever has a first end integral with the body portion. The lever also has a second end. The lever further has an engagement surface located intermediate the first end and the second end. The second end of the lever is actuable to urge the engagement surface against the proximal end of the femoral canal preparation instrument to secure the proximal end of the femoral canal preparation instrument within the bore.

19 Claims, 6 Drawing Sheets

(56) References Cited

U.S. PATENT DOCUMENTS

| | | |
|---|---|---|
| 7,425,214 B1 | 9/2008 | McCarthy |
| 7,981,161 B2 | 7/2011 | Choi |
| 8,449,619 B2 * | 5/2013 | Metcalfe ............... A61F 2/4684 623/22.11 |
| 9,439,785 B2 * | 9/2016 | Huddle ................. A61F 2/4684 |
| 11,344,437 B2 * | 5/2022 | Bailey ................ A61B 17/1659 |
| 11,602,359 B2 * | 3/2023 | Clements ............ A61B 17/162 |
| 2003/0088316 A1 | 5/2003 | Ganjianpour |
| 2004/0054419 A1 | 3/2004 | Serra |
| 2004/0267267 A1 * | 12/2004 | Daniels ............. A61B 17/1617 623/22.42 |
| 2006/0241625 A1 * | 10/2006 | Metcalfe ............. A61B 17/162 606/79 |
| 2008/0133023 A1 | 6/2008 | Schlotterback |
| 2012/0259338 A1 * | 10/2012 | Carr ..................... A61F 2/4684 606/80 |
| 2012/0259424 A1 * | 10/2012 | Hood ................... A61F 2/4684 623/23.35 |
| 2012/0290099 A1 | 11/2012 | Gibson |
| 2015/0018961 A1 * | 1/2015 | Huddle ................. A61F 2/4684 623/22.4 |
| 2019/0117412 A1 * | 4/2019 | Zimmerman ...... A61B 17/1668 |
| 2019/0231540 A1 * | 8/2019 | Kim .......................... A61F 2/36 |
| 2020/0276029 A1 * | 9/2020 | Bailey ............... A61B 17/1668 |
| 2022/0233337 A1 * | 7/2022 | Dmuschewsky ..... A61F 2/3601 |
| 2022/0241092 A1 * | 8/2022 | Board ................... A61F 2/4607 |
| 2022/0249256 A1 * | 8/2022 | Amaral ............. A61B 17/1668 |
| 2022/0346976 A1 * | 11/2022 | Naylor ................. A61F 2/3662 |

FOREIGN PATENT DOCUMENTS

| | | | |
|---|---|---|---|
| EP | 1013242 A2 | 6/2000 | |
| FR | 2788429 A1 | 7/2000 | |
| FR | 3043545 A1 | 5/2017 | |
| JP | 2003010215 A | 1/2003 | |
| JP | 2012165889 A | 9/2012 | |
| JP | 2013094331 A * | 5/2013 | ........... A61F 2/4684 |
| JP | 5859810 B2 | 2/2016 | |

* cited by examiner

TRIAL NECK AND METHOD

BACKGROUND

The present specification relates to a trial neck and to a method of attaching a trial neck to a femoral canal preparation instrument.

Hip replacement is a surgical procedure in which the hip joint is replaced by a prosthetic implant. Total replacement of the hip joint involves installing an acetabular cup implant in the acetabulum of a patient and installing a prosthetic in the femur of the patient. The prosthetic typically includes a stem, which is received in the medullary canal of the femur, and a head having a bearing surface which is received in the acetabulum or acetabular cup implant. The prosthetic typically also includes a neck which extends between a proximal end of the stem and the head.

Successful hip replacement surgery requires correct positioning and alignment of the acetabular cup implant as well as the prosthetic itself. Misalignment and/or the selection of an inappropriately sized acetabular cup implant and/or the prosthetic may result is restricted movement of the prosthetic and/or accelerated wear and tear of the bearing surfaces of the acetabular cup implant and the bearing surface of the head. Various factors are involved in achieving this correct positioning and alignment. At least some of these factors relate to the neck of the prosthetic. These factors may include, for instance, the length of the neck (offset), and an angular orientation of the neck relative to the stem.

Hip replacement surgery usually involves trialling the various components of the acetabular cup implant and the prosthetic. As part of this, various sizes of broach/reamer may be used to prepare the medullary canal of the femur. Once the broach/reamer is inserted in the femur, a trial neck and trial head may also be attached to the broach/reamer, in order to evaluate whether a prosthetic having a neck and head of that type (e.g. in terms of the size and offset of the neck) would appropriate for the patient.

After the surgeon is satisfied that the chosen combination of broach/reamer, trial neck and trial head are correctly positioned and aligned, they may be removed and replaced with the implant itself.

SUMMARY

Aspects of the present disclosure are set out in the accompanying independent and dependent claims. Combinations of features from the dependent claims may be combined with features of the independent claims as appropriate and not merely as explicitly set out in the claims.

According to an aspect of the present disclosure, there is provided a trial neck for hip surgery, the trial neck comprising:
a body portion including a bore for receiving a proximal end of a femoral canal preparation instrument;
an elongate neck extending from the body portion;
a locking mechanism comprising a lever having:
a first end integral with the body portion;
a second end; and
an engagement surface located intermediate the first end and the second end,
wherein the second end of the lever is actuable to urge the engagement surface against the proximal end of the femoral canal preparation instrument to secure the proximal end of the femoral canal preparation instrument within the bore.

A lever of the locking mechanism of the trial neck may provide a secure way of attaching the trial neck to a femoral canal preparation instrument. The lever can allow a sufficient securing force to be applied to the femoral canal preparation instrument within the bore, while also allowing fine adjustments to be made.

The locking mechanism may further include an actuation member for engaging with the second end of the lever to actuate the lever. This can provide a convenient way of operating the lever.

The trial neck of claim 2 may include a further bore. The actuation member may extend within the further bore. The further bore may extend within the elongate neck.

The further bore may extend substantially parallel to a longitudinal axis of the elongate neck.

A proximal end of the elongate neck may have an opening leading to the further bore. A proximal end of the actuation member may include a connection feature for connecting a tool to the actuation member for actuating the actuation member.

The proximal end of the elongate neck may be configured to be attached to a trial head.

The further bore may have a threaded surface. The actuation member may have a threaded surface for engaging with the threaded surface of the further bore to allow the actuation member to be rotated to move the actuation member along the further bore to engage with the second end of the lever. The threaded engagement of the actuation member can allow fine adjustments to be made to the position of the lever.

The trial neck may have a window for viewing the actuation member within the further bore. This can be useful also for cleaning of the trial neck between surgical procedures.

The second end of the lever may be located within the elongate neck.

The first end of the lever may be located at a lateral side of the trial neck.

The engagement surface of the lever may be curved to conform with a curved outer surface of the proximal end of the femoral canal preparation instrument.

An inner surface of the bore may have a profiled surface for engaging with a corresponding profiled outer surface of the proximal end of the femoral canal preparation instrument to prevent rotation of the femoral canal preparation instrument with respect to the trial neck about a longitudinal axis of the femoral canal preparation instrument.

The lever may include at least one dog leg bend. This can allow the lever arm provided by the lever to be optimised.

The femoral canal preparation instrument may, for example, be a reamer, a trial stem, or a broach.

According to another aspect of the present disclosure, there is provided a surgical kit comprising:
a trial neck of the kind set out above; and
a femoral canal preparation instrument.

The proximal end of the femoral canal preparation instrument may include a circumferential lip or groove for engagement with the engagement surface of the locking mechanism of the trial neck. The engagement surface may catch against the lip or groove when the locking mechanism is locked, to resist removal of the proximal end of the femoral canal preparation instrument from the bore.

The femoral canal preparation instrument may, for example, be a reamer, a trial stem, or a broach.

According to a further aspect of the present disclosure, there is provided a method of attaching a trial neck to a femoral canal preparation instrument, the trial neck comprising:

a body portion including a bore for receiving a proximal end of a femoral canal preparation instrument;

an elongate neck extending from the body portion;

a locking mechanism comprising a lever having:
  a first end integral with the body portion;
  a second end; and
  an engagement surface located intermediate the first end and the second end, wherein the second end of the lever is actuable to urge the engagement surface against the proximal end of the femoral canal preparation instrument to secure the proximal end of the femoral canal preparation instrument within the bore, the method comprising:

inserting the proximal end of the femoral canal preparation instrument into the bore; and actuating the second end of the lever to urge the engagement surface against the proximal end of the femoral canal preparation instrument.

A lever of the locking mechanism of the trial neck may provide a secure way of attaching the trial neck to a femoral canal preparation instrument. The lever can allow a sufficient securing force to be applied to the femoral canal preparation instrument within the bore, while also allowing fine adjustments to be made.

The method may include engaging an actuation member of the locking mechanism with the second end of the lever to actuate the lever. This can provide a convenient way of operating the lever.

A proximal end of the actuation member may include a connection feature. The method may further include connecting a tool to the actuation member to the connection feature for actuating the actuation member.

The method may further include viewing the actuation member through a window in the elongate neck of the trial neck.

The engagement surface of the lever may be curved to conform with a curved outer surface of the proximal end of the femoral canal preparation instrument.

The femoral canal preparation instrument may, for example, be a reamer, a trial stem, or a broach.

BRIEF DESCRIPTION OF THE DRAWINGS

Embodiments of this disclosure will be described hereinafter, by way of example only, with reference to the accompanying drawings in which like reference signs relate to like elements and in which.

DETAILED DESCRIPTION

Figure 1:
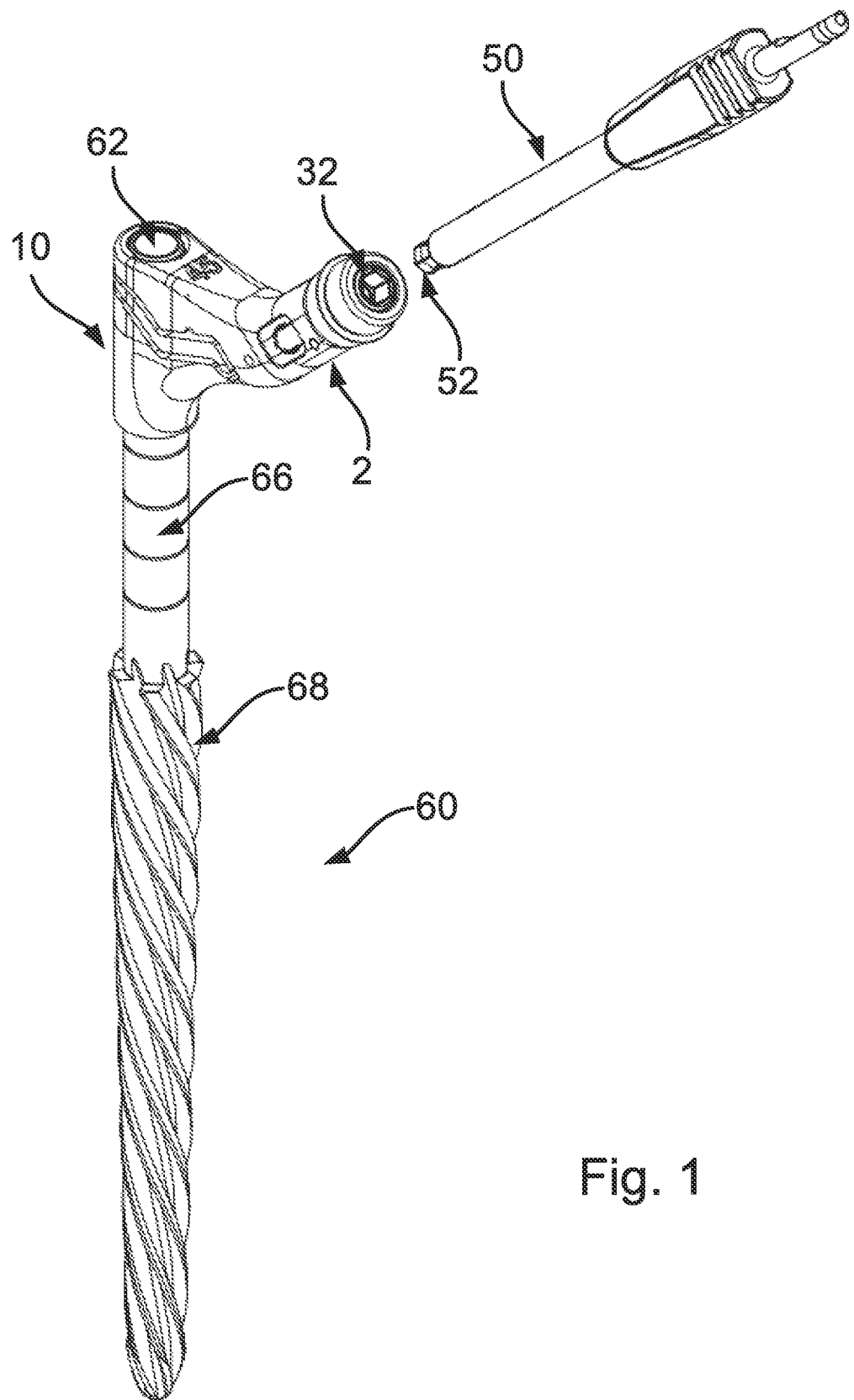
FIG. 1 shows a trial neck attached to a femoral canal preparation instrument, such as a reamer, according to an embodiment of this disclosure.
Figure 2:
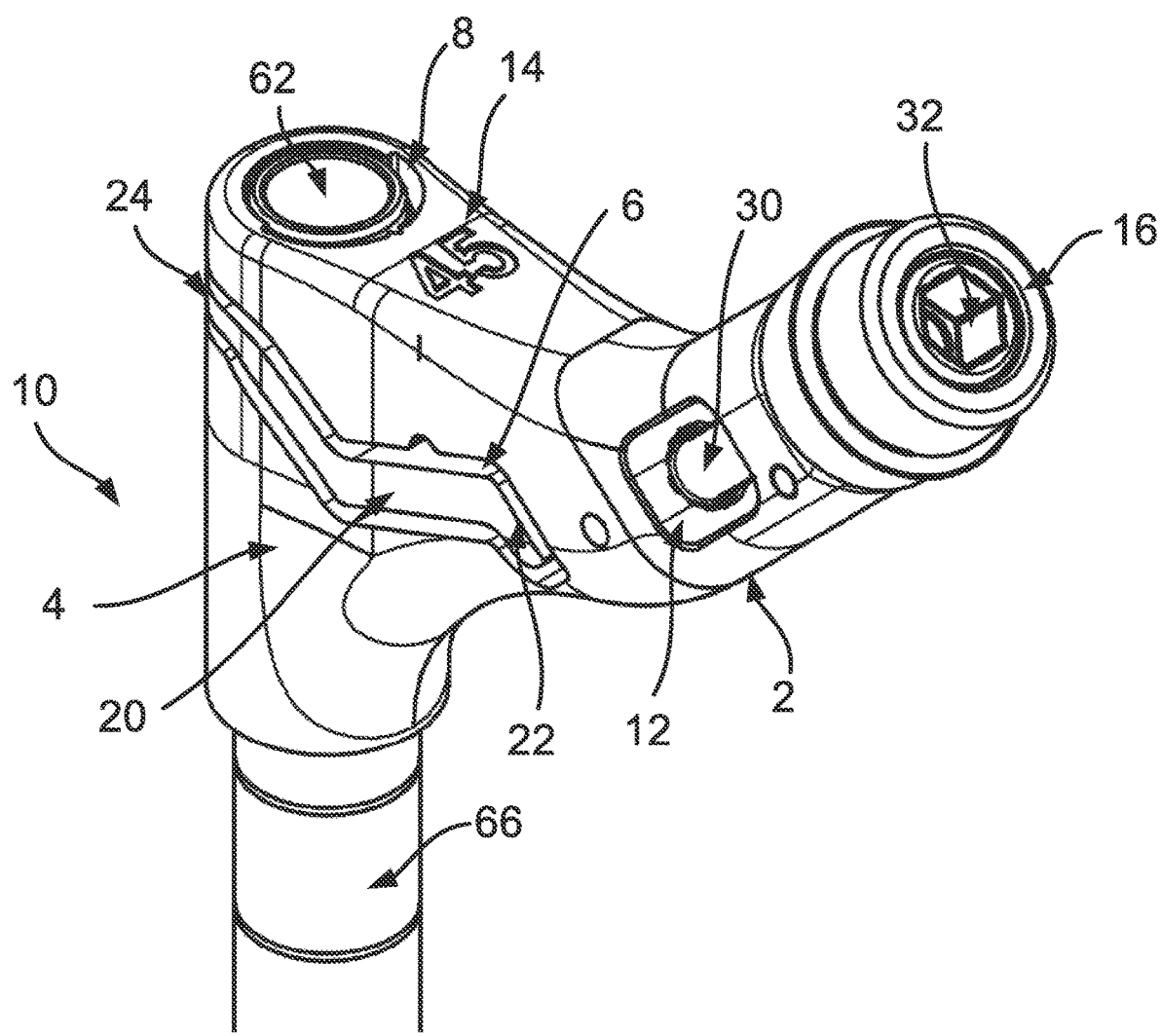
FIG. 2 shows another view of the trial neck of FIG. 1.
Figure 3:
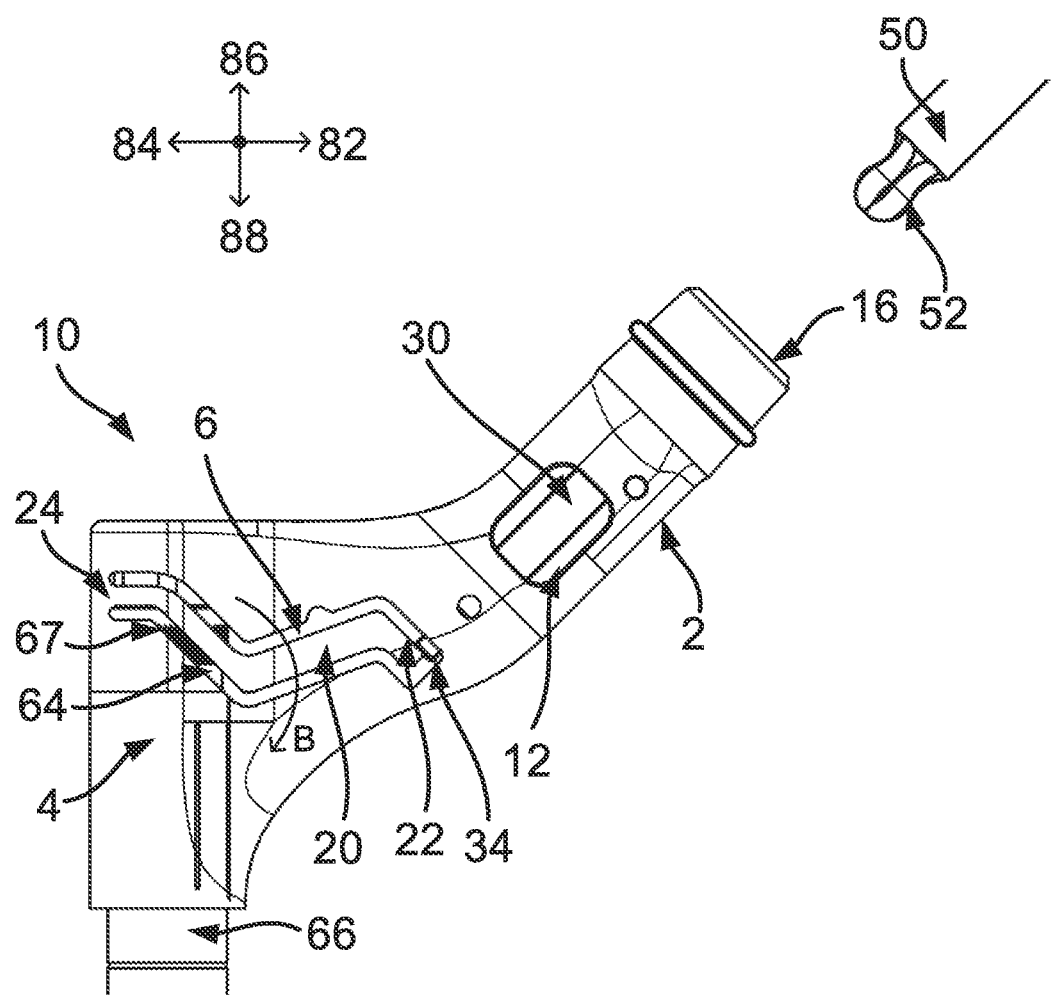
FIG. 3 shows an anterior view of the trial neck of FIG. 1.
Figure 4A:
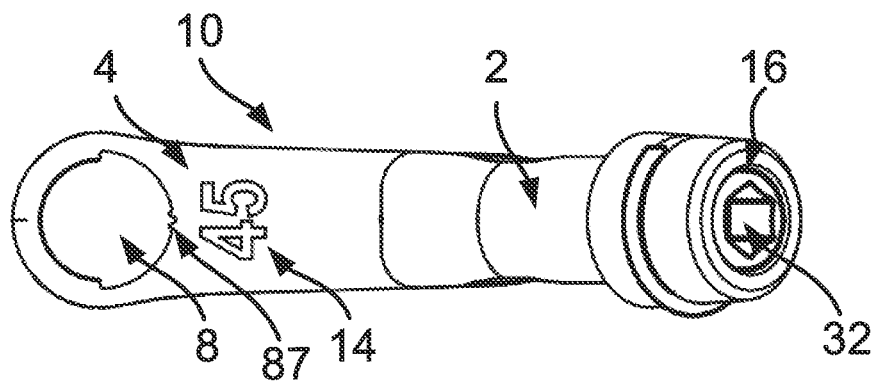
FIG. 4A shows a superior view of the trial neck of FIG. 1.
Figure 4B:
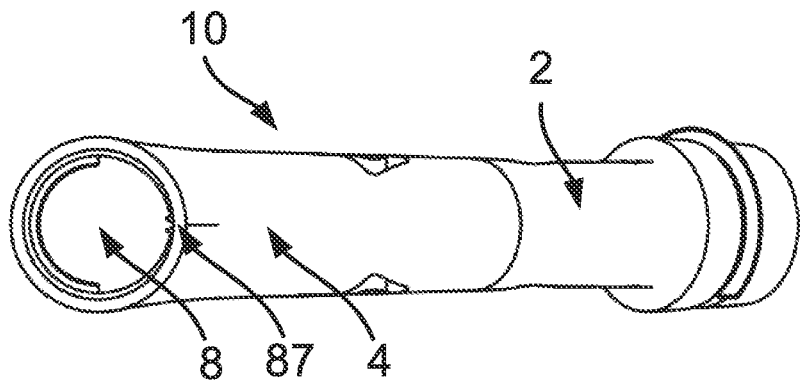
FIG. 4B shows an inferior view of the trial neck of FIG. 1.
Figure 4C:
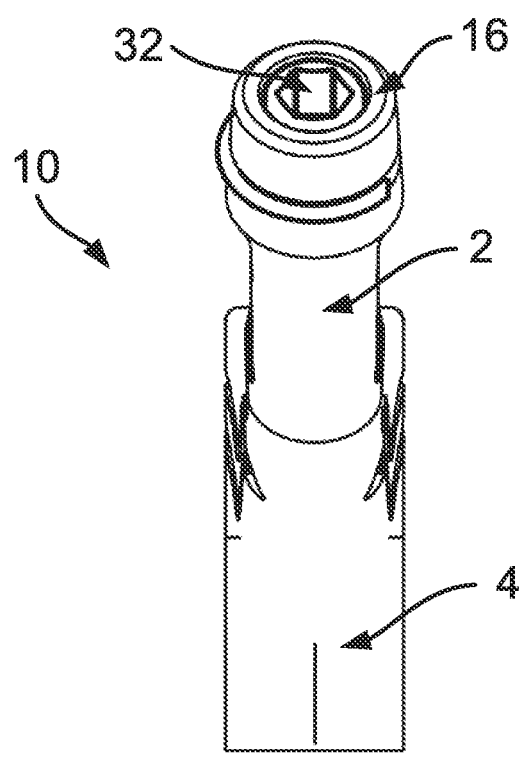
FIG. 4C shows a medial view of the trial neck of FIG. 1.

Embodiments of this disclosure are described in the following with reference to the accompanying drawings.

Various views of a trial neck 10 and a femoral canal preparation instrument according to an embodiment of this disclosure are shown in FIGS. 1 to 7. In the Figures, the following directions are indicated:

medial direction 82;
lateral direction 84;
superior direction 86; and
inferior direction 88

The femoral canal preparation instrument may, for example, be a reamer, a trial stem, or a broach. In the following description of FIGS. 1 to 7, the femoral canal preparation instrument comprises a reamer 60. However, it will be appreciated that in other embodiments, the femoral canal preparation instrument may be one of the other instruments noted above and may have a proximal end that is configured similarly to the proximal end 64 of the reamer 60.

The trial neck 10 has a body portion 4. The body portion 4 includes a bore 8. The bore 8 may be a blind bore (closed at its proximal end), although in the embodiment shown in the Figures it is an open bore, which passes completely through the body portion 4. The bore 8 can receive the proximal end of a reamer 60, for attaching the reamer 60 to the trial neck 10.

The reamer 60 itself may be in the form of an elongate shaft (e.g. see FIG. 1) and may have a cutting surface 68 located distally. The reamer 60 may also have an intermediate part 66 located proximally with respect to the cutting surface 68. The reamer 60 has a proximal end 64. The proximal end 64 may be located proximally with respect to the cutting surface 68 and/or the intermediate part 66. The proximal end 64 may be substantially cylindrical, with a circular cross section, although this is not essential. The proximal end 64 may be inserted into the bore 8 of the trial neck 10 for attaching the reamer 60 to the trial neck, as will be described in more detail below.

Figure 5:
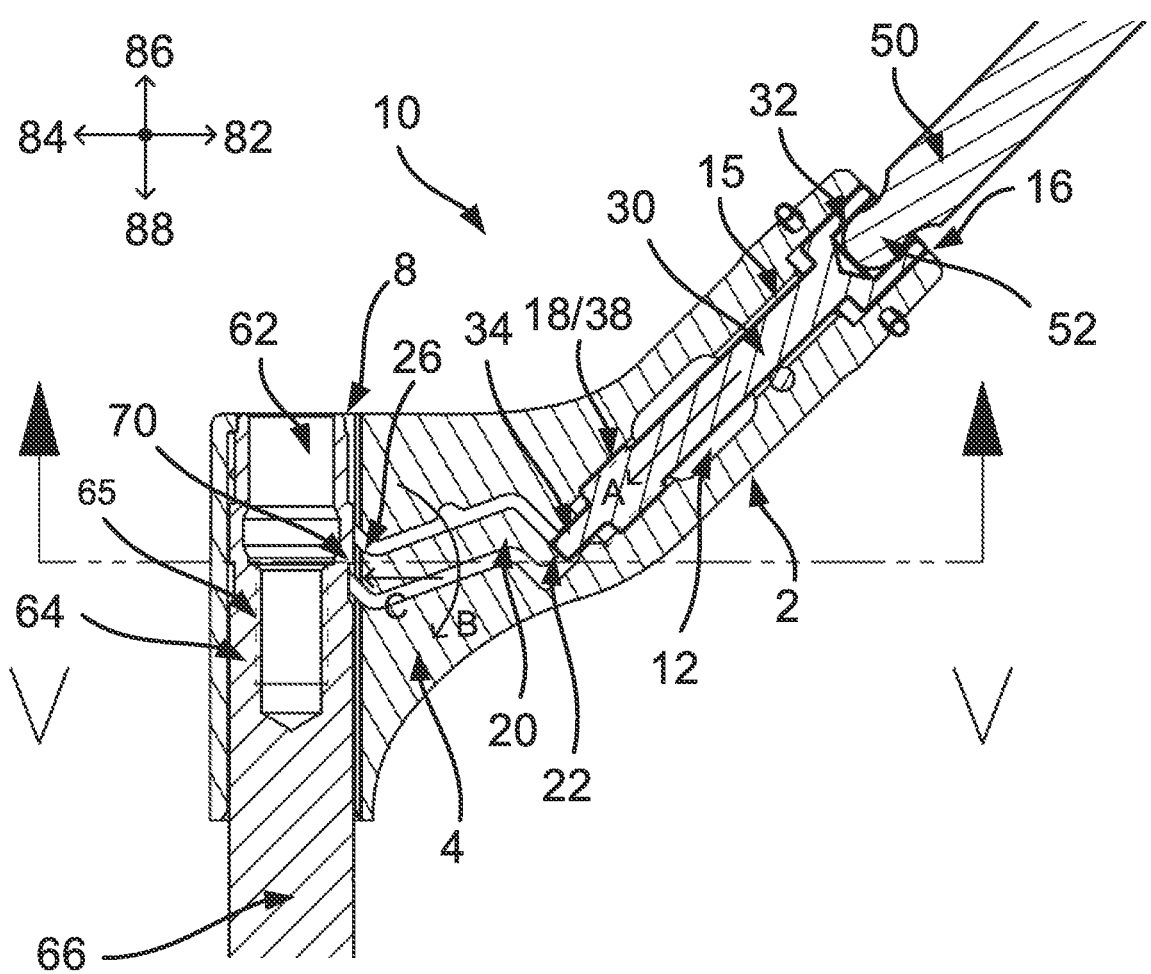
FIG. 5 shows a cross section of the trial neck of FIG. 1.

As can be seen in FIG. 5, the proximal end 64 of the reamer 60 may include a number of features. For instance, the proximal end 64 may have a connection feature 62, such as a profiled bore, for attaching the reamer 60 to a reamer driver. The bore of the connection feature 62 may include an internal screw thread 65, to aid attachment of the reamer driver. In embodiments in which the bore 8 extends completely through the body portion 8, the reamer driver may be attached to the reamer 60 using the connection feature 62 even when the trial neck 10 is attached to the reamer 60.

The proximal end 64 of the reamer 60 also may include a circumferential lip or groove 70 for engagement with an engagement surface of the locking mechanism of the trial neck 10 to be described in detail below. As can be seen in FIG. 5, the lip or groove 70 may be formed by an edge of a circumferential part of the proximal end 64 of the reamer 60 that has a stepped increase (or decrease) in the radius of the proximal end 64.

In some embodiments, the reamer 60 may include a surface which is angled to conform with the engagement surface of the locking mechanism, at the angle at which the engagement surface contacts the reamer 60. The angled surface may comprise a circumferential (e.g. annular) indentation which extends around the reamer 60 (in much the same way as the lip or groove 70). In this way, the contacting surface areas of the reamer 60 and the engagement surface can be maximised, and potential damage to the surface of the reamer 60 (caused by the engagement surface "digging in to" the reamer 60) can be avoided.

The trial neck 10 also has an elongate neck 2. The elongate neck 2 extends from the body portion 4. The elongate neck 2 extends at a non-zero angle relative to a longitudinal axis of the bore 8. A proximal end 16 of the elongate neck 2 may be configured (i.e. include connection feature(s)) to be attached to a trial head.

The trial neck 10 may include one or more external indicia 14 for indicating information about the type, or dimensions of the trial neck 10. In the embodiment shown in the figures, one such indicium 14 is located on a proximal (superior) surface of the trial neck 10, although other locations for such indicia are possible.

As noted previously, the proximal end 64 of the reamer 60 may be received within the bore 8 for attaching the reamer 60 to the trial neck 10. According to embodiments of this disclosure, the trial neck 10 includes a locking mechanism. The locking mechanism can be used to lock the proximal end 64 of the reamer 60 within the bore 8, so as to prevent movement of the reamer 60 with respect to the trial neck 10 and/or inadvertent decoupling of the trial neck 10 from the reamer 60.

The locking mechanism comprises a lever 20. The lever 20 has a first end 24, a second end 22 and an engagement surface 26. The first end 24 may be located laterally with respect to the engagement surface 26 and the second end 22. The engagement surface 26 may be located laterally with respect to the second end 22.

The first end 24 is integral with the body portion 4. As may be appreciated from a review of FIGS. 2, 3, 6 and 7, the first end 24 of the lever 20 may comprise a pair of arms which each extend around the bore 8 to join with the body portion 4 at a point located generally laterally on the trial neck 10. The point(s) at which the (pair of arms of) the first end 24 join the body portion 4 may form the hinge of a live spring.

The second end 22 in this embodiment is located within the elongate neck 2 of the trial neck 10, although it may be located in the body portion 4. Locating the second end 22 within the elongate neck 2 can allow the second end 22 sufficiently far away from the engagement surface 26 to allow the mechanical advantage provided by the lever 20 to be improved, compared to the location of the second end 22 of the lever 20 within the body portion 4.

The engagement surface 26 is located intermediate the first end 24 and the second end 22. The engagement surface 26 in this embodiment is located adjacent a side wall of the bore 8, allowing the engagement surface 26 to come in to contact with and urge against the proximal end 64 of the reamer 60 to secure the proximal end 64 of the reamer 60 within the bore 8 when the lever 20 is actuated.

In the present embodiment, the aforementioned pair of arms of the lever 20, which extend round the bore 8, extend generally in the lateral direction 84 from the part of the lever 20 including the engagement surface 26, so as to join with the body portion 4 at the first end 24. The part of the lever 20 between the engagement surface 26 and the second end 22 may comprise a single solid piece, which bifurcates at the engagement surface 26 to form the pair of arms. The lever my thus be substantially fork-shaped or Y-shaped when viewed along the along the longitudinal axis of the bore 8.

As can be seen from the Figures, the part of the lever 20 between the engagement surface 26 and the second end 22 may include a number of dog leg type bends. This can allow a mechanical advantage to be gained from the actuation of the second end 22 of the lever 20 as described below, while also allowing the lever 20 to navigate the aforementioned non-zero angle between the elongate neck 2 and the longitudinal axis of the bore 8.

As can also be seen from the Figures, the lever 20 may reside in a slot formed in the side walls of the trial neck 10. The slot may be dimensioned with enough clearance to ensure that the lever 20 can be actuated without fouling the sides of the slot.

In some embodiments, the locking mechanism also includes an actuation member 30. The actuation member 30 can be used to actuate the second end of the lever 20.

In the present embodiment, the trial neck 10 has a further bore 15 within which the actuation member 30 extends. The further bore 15 may extend substantially parallel to a (longitudinal) neck axis of the elongate neck 2. The further bore 15 may terminate at the proximal end 16 of the elongate neck 2. An opening to the further bore 15 located in this embodiment at the proximal end 16 of the elongate neck 2 may allow access to the actuation member 30. A proximal end of the actuation member 30 may comprise a connection feature 32 for connecting a corresponding connection feature 52 of a tool 50 to the actuation member 30 for actuating the actuation member 30. In some embodiments, a trial head, which is attachable to the proximal end 16 of the elongate neck 2, may include an opening or aperture, which passes through the trial head so as to provide access to the connection feature 32 for operating the actuation member 30. For instance, the tool 50 may be inserted through the opening or aperture in the trial head, to couple the connection feature 52 to the connection feature 32.

To operate the actuation member 30, it may be moved along the further bore 15 (in the direction shown by the arrow "A" in FIG. 5, which in this embodiment is substantially parallel to the longitudinal axis of the elongate neck 2) towards the second end 22 of the lever 20. A tip 34 may thus come into contact with the second end 22 of the lever 20 thereby to deflect the lever 20. This causes the lever 20 to rotate around the first end 24 of the lever 20 (in the direction shown by the arrow "B" in FIG. 5). This in turn causes the engagement surface 26 to urge against the proximal end 64 of the reamer 60 to lock the proximal end 62 within the bore 8.

The further bore 15 may have a threaded surface 18 for engaging with a corresponding threaded surface 38 of the actuation member 30. Rotation of the actuation member 30 within the further bore 15 (e.g. using the tool 50) can cause the actuation member to move back and forth within the further bore 15, and along the direction "A" as noted above, thereby to operate the lever 20.

In some embodiments, the trial neck may include one or more windows. For instance, the trial neck 10 in the embodiment shown in the drawings has a window 12 located in the elongate neck 2. The window 12 may open out onto both an anterior and a posterior surface of the elongate neck 10. The window 12 may allow the actuation member 30 to be viewed within the further bore 15. This can allow the position of the actuation member 30 within the further bore 15 to be determined by inspection. The window(s) 12 may also allow improved access to the interior of the trial neck 10 (particularly the further bore 15) for cleaning operations. Note that the aforementioned slot, within which the lever 20 may be located, may similarly allow access to the interior of the trial neck 10 for improved cleaning operations.

Figure 6:
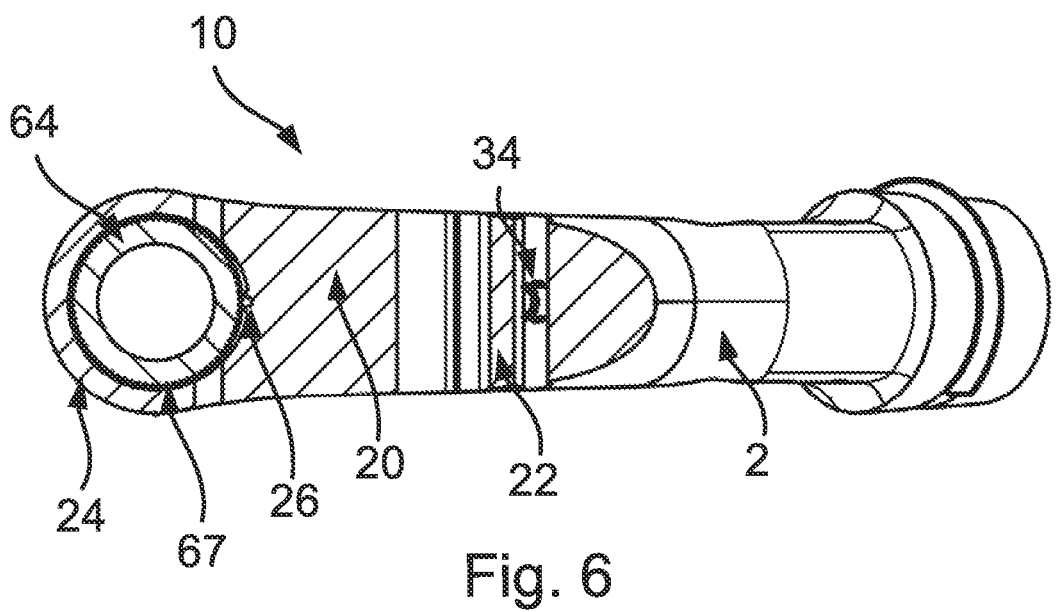
FIG. 6 shows another cross section of the trial neck of FIG. 1, through the plane V-V indicated in FIG. 5.
Figure 7:
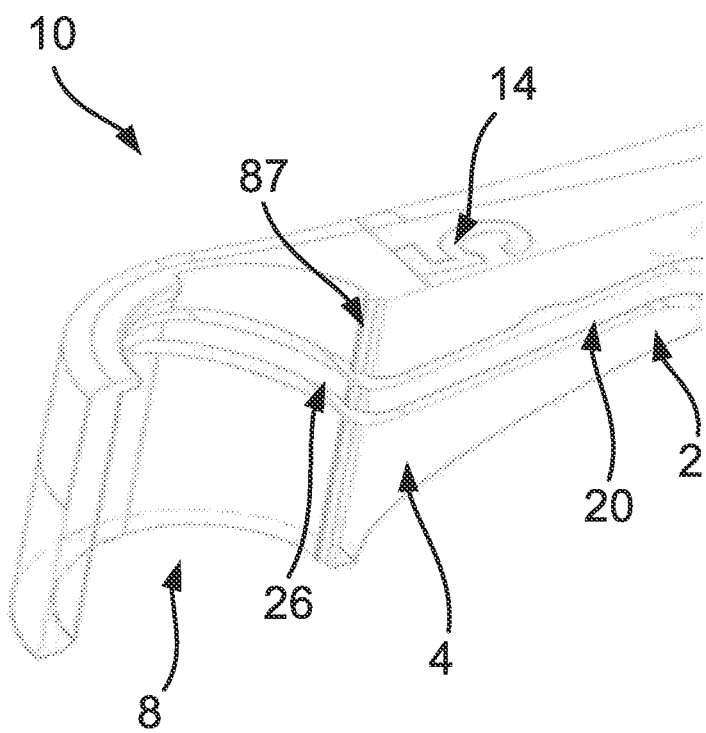
FIG. 7 is a cross section of the trial neck of FIG. 1, showing a profiled surface of the bore of the trial neck, for engaging with a corresponding profile surface of the femoral canal preparation instrument.

In some embodiments, the engagement surface 26 of the lever 20 may be curved (an example of this in the present embodiment can be seen in FIGS. 6 and 7. This can allow the engagement surface substantially to conform with a curved outer surface of the proximal end 64 of the reamer 60. By conforming with the curved outer surface of the proximal end 64 of the reamer 60, the size of the area of engagement between the engagement surface 26 and the proximal end 64 may be increased, for a more secure connection between the trial neck 10 and the reamer 60. Note that a part of the engagement surface 26 located on the aforementioned pair of arms of the lever 20 may form at least part of the curved engagement surface 26 in some embodiments.

The locking mechanism described above generally opposes movement of the reamer 60 along the longitudinal axis of the bore 8, thereby to prevent inadvertent movement of the trial neck 10 relative to the reamer 60 and/or to prevent inadvertent removal of the proximal end of the reamer 60 from the bore 8. In some embodiments, the trial neck 10 and/or the reamer 60 may include features for opposing rotation of the reamer 60 withing the bore 8 (i.e. around the longitudinal axis of the bore 8). Note that even in the absence of such additional features, the frictional force associated with the urging of the engagement surface 26 against the proximal end of the reamer 60 may to some extent also oppose rotation of the reamer 60 within the bore 8.

In the embodiment shown in the Figures (see, in particular, FIGS. 4A, 4B and 7), an inner surface of the bore 8 has a profiled surface 87 for engaging with a corresponding profiled outer surface 67 (see FIGS. 3 and 6) of the proximal end 64 of the reamer 60. Engagement of these profiled surfaces 67/87 can resist rotation of the reamer 60 with respect to the trial neck 10 about a longitudinal axis of the bore 8/reamer 60 as noted above. The profiled surface 67 on the reamer 60 may extend completely around the circumference of the proximal end 64 of the reamer 60 (as can be seen in FIG. 6) so that part of the profiled surface 67 may be presented to the profiled surface 87 of the trial neck 10, irrespective of the orientation of the proximal end 64 of the reamer 60 when it is first inserted into the bore 8.

As may be seen in FIG. 7, the profiled surface 87 need not extend around the circumference of the bore 8, but instead may be present only on a segment of the bore 8 (in FIG. 7, the segment including the profiled surface 87 is a most medially located part of the inner surface of the bore 8). As may also be seen in FIG. 7, the profiled surface 87 may extend completely along a length of the inner surface of the bore 15. In the embodiment shown in the Figures, the profiled surface 87 extends from a proximal end of the bore 8 to a distal end of the bore 8, and part of the profiled surface 87 is located on the engagement surface 26. However, it is also envisaged that the profiled surface 87 may only be located on the engagement surface 26.

As described above, the proximal end 64 of the reamer 60 may include a circumferential lip or groove 70 for engagement with an engagement surface of the locking mechanism of the trial neck 10. As can be seen in FIG. 5, the lip or groove 70 may be formed by an edge of a circumferential part of the proximal end 64 of the reamer 60 that has a stepped increase (or decrease) in the radius of the proximal end 64. In some embodiments, the profiled surface 67 may be located on this lip and/or in this groove 70, for engagement with the (part of) the profiled surface 87 on the engagement surface 26 of the lever 20. Note that in some embodiments, the engagement surface may catch against the lip or groove 70 (e.g. the part of the lever 20 including the engagement surface 26 may slot into the groove 70) when the locking mechanism is locked, to resist removal of the proximal end 64 of the reamer 60 from the bore 8. In this way, in addition to the frictional force applied by the engagement surface 26, the engagement surface 26 may physically block the removal of the proximal end 64 of the reamer 60 from the bore 8.

The profiled surfaces 67/87 may comprise correspondingly shaped splines, which run substantially parallel to the longitudinal axes of the reamer 60 and the bore 8. Other kinds of profiled surfaces may be used. Note that the (part of) the profiled surface 87 on the engagement surface 26 may form a tooth or teeth, which engage with the profiled surface 67 on the proximal end 64 of the reamer 60 (e.g. see FIG. 6).

According to an embodiment of this disclosure, there may be provided a method of attaching a trial neck (e.g. a trial neck 10 of the kind described above) to a femoral canal preparation instrument (such as the reamer 60). The method may include inserting the proximal end 64 of the femoral canal preparation instrument (e.g. reamer 60) into the bore 8 of the trial neck 10. The method may also include actuating the second end 22 of the lever 20 to urge the engagement surface 26 against the proximal end 64 of the femoral canal preparation instrument (e.g. reamer 60).

As noted above, the method may include actuating the second end 22 of the lever 20 using an actuation member, e.g. the actuation member 30. The method may also include connecting a tool (e.g. the tool 50) to the connection feature 32 of the actuation member 30 for actuating the actuation member 30. While using the trial neck 10, the method may also include viewing the actuation member 30 through a window (e.g. the window 12) in the elongate neck 2 of the trial neck 10. The method may further include cleaning the trial neck 10 before it is used (again). The window 12 may assist in this cleaning, by allowing improved access to the further bore 15 within which the actuation member 30 may be located.

According to an embodiment of this disclosure, there may be provided a surgical kit. The surgical kit may include a trial neck 10 of the kind described above. The surgical kit may also include a femoral canal preparation instrument (e.g. a reamer 60) of the kind described above. It is envisaged that the kit may include further components (e.g. one or more differently sized trial necks of the kind described above, one or more different kinds of reamer, one or more trial heads, and/or any other components).

Accordingly, there has been described a trial neck for hip surgery and a method of attaching a trial neck to a femoral canal preparation instrument. The trial neck includes a body portion including a bore for receiving a proximal end of a femoral canal preparation instrument. The trial neck also includes an elongate neck extending from the body portion. The trial neck further includes a locking mechanism comprising a lever. The lever has a first end integral with the body portion. The lever also has a second end. The lever further has an engagement surface located intermediate the first end and the second end. The second end of the lever is actuable to urge the engagement surface against the proximal end of the femoral canal preparation instrument to secure the proximal end of the femoral canal preparation instrument within the bore.

Aspects of the present disclosure are set out in the following series of numbered clauses.

1. A trial neck for hip surgery, the trial neck comprising:
   a body portion including a bore for receiving a proximal end of a femoral canal preparation instrument;
   an elongate neck extending from the body portion;
   a locking mechanism comprising a lever having:
      a first end integral with the body portion;
      a second end; and
      an engagement surface located intermediate the first end and the second end, wherein the second end of the lever is actuable to urge the engagement surface against the proximal end of the femoral canal preparation instrument to secure the proximal end of the femoral canal preparation instrument within the bore.
2. The trial neck of clause 1, wherein the locking mechanism further comprises an actuation member for engaging with the second end of the lever to actuate the lever.
3. The trial neck of clause 2 comprising a further bore, wherein the actuation member extends within the further bore.
4. The trial neck of clause 3, wherein the further bore extends within the elongate neck.
5. The trial neck of clause 4, wherein the further bore extends substantially parallel to a longitudinal axis of the elongate neck.
6. The trial neck of clause 4 of clause 5, wherein a proximal end of the elongate neck has an opening leading to the further bore, and wherein a proximal end of the actuation member comprises a connection feature for connecting a tool to the actuation member for actuating the actuation member.
7. The trial neck of clause 6, wherein the proximal end of the elongate neck is configured to be attached to a trial head.
8. The trial neck of any of clauses 3 to 7, wherein:
the further bore has a threaded surface, and
wherein the actuation member comprises a threaded surface for engaging with the threaded surface of the further bore to allow the actuation member to be rotated to move the actuation member along the further bore to engage with the second end of the lever.
9. The trial neck of any of clauses 3 to 8, comprising a window for viewing the actuation member within the further bore.
10. The trial neck of any preceding clause wherein the second end of the lever is located within the elongate neck.
11. The trial neck of any preceding clause, wherein the first end of the lever is located at a lateral side of the trial neck.
12. The trial neck of any preceding clause, wherein the engagement surface of the lever is curved to conform with a curved outer surface of the proximal end of the femoral canal preparation instrument.
13. The trial neck of any preceding clause, wherein an inner surface of the bore has a profiled surface for engaging with a corresponding profiled outer surface of the proximal end of the femoral canal preparation instrument to prevent rotation of the femoral canal preparation instrument with respect to the trial neck about a longitudinal axis of the femoral canal preparation instrument.
14. The trial neck of any preceding clause, wherein the lever includes at least one dog leg bend.
15. A surgical kit comprising:
a trial neck according to any preceding clause; and
a femoral canal preparation instrument.
16. The kit of clause 15, wherein the proximal end of the femoral canal preparation instrument includes a circumferential lip or groove for engagement with the engagement surface of the locking mechanism of the trial neck.
17. A method of attaching a trial neck to a femoral canal preparation instrument, the trial neck comprising:
a body portion including a bore for receiving a proximal end of a femoral canal preparation instrument;
an elongate neck extending from the body portion;
a locking mechanism comprising a lever having:
a first end integral with the body portion;
a second end; and
an engagement surface located intermediate the first end and the second end,
wherein the second end of the lever is actuable to urge the engagement surface against the proximal end of the femoral canal preparation instrument to secure the proximal end of the femoral canal preparation instrument within the bore,
the method comprising:
inserting the proximal end of the femoral canal preparation instrument into the bore; and
actuating the second end of the lever to urge the engagement surface against the proximal end of the femoral canal preparation instrument.
18. The method of clause 17, comprising engaging an actuation member of the locking mechanism with the second end of the lever to actuate the lever.
19. The method of clause 18, wherein a proximal end of the actuation member comprises a connection feature, and wherein the method further comprises connecting a tool to the actuation member to the connection feature for actuating the actuation member.
20. The method of any of clauses 17 to 19, further comprising viewing the actuation member through a window in the elongate neck of the trial neck.

Although particular embodiments of this disclosure have been described, it will be appreciated that many modifications/additions and/or substitutions may be made within the scope of the claims.

The invention claimed is:
1. A trial neck for hip surgery, the trial neck comprising:
a body portion including a bore for receiving a proximal end of a femoral canal preparation instrument;
an elongate neck extending from the body portion;
a locking mechanism comprising a lever having:
a first end integral with the body portion;
a second end; and
an engagement surface located intermediate the first end and the second end,
wherein the second end of the lever is actuable to urge the engagement surface against the proximal end of the femoral canal preparation instrument to secure the proximal end of the femoral canal preparation instrument within the bore, and wherein the second end of the lever is located within the elongate neck.
2. The trial neck of claim 1, wherein the locking mechanism further comprises an actuation member for engaging with the second end of the lever to actuate the lever.
3. The trial neck of claim 2 comprising a further bore, wherein the actuation member extends within the further bore.
4. The trial neck of claim 3, wherein the further bore extends within the elongate neck.
5. The trial neck of claim 4, wherein the further bore extends substantially parallel to a longitudinal axis of the elongate neck.
6. The trial neck of claim 4, wherein a proximal end of the elongate neck has an opening leading to the further bore, and wherein a proximal end of the actuation member comprises a connection feature for connecting a tool to the actuation member for actuating the actuation member.
7. The trial neck of claim 6, wherein the proximal end of the elongate neck is configured to be attached to a trial head.
8. The trial neck of claim 3, wherein:
the further bore has a threaded surface, and
wherein the actuation member comprises a threaded surface for engaging with the threaded surface of the further bore to allow the actuation member to be rotated to move the actuation member along the further bore to engage with the second end of the lever.

9. The trial neck of claim 3, comprising a window for viewing the actuation member within the further bore.

10. The trial neck of claim 1, wherein the first end of the lever is located at a lateral side of the trial neck.

11. The trial neck of claim 1, wherein the engagement surface of the lever is curved to conform with a curved outer surface of the proximal end of the femoral canal preparation instrument.

12. The trial neck of claim 1, wherein an inner surface of the bore has a profiled surface for engaging with a corresponding profiled outer surface of the proximal end of the femoral canal preparation instrument to prevent rotation of the femoral canal preparation instrument with respect to the trial neck about a longitudinal axis of the femoral canal preparation instrument.

13. The trial neck of claim 1, wherein the lever includes at least one dog leg bend.

14. A surgical kit comprising:
a trial neck for hip surgery, the trial neck comprising:
    a body portion including a bore for receiving a proximal end of a femoral canal preparation instrument;
    an elongate neck extending from the body portion;
    a locking mechanism comprising a lever having:
        a first end integral with the body portion;
        a second end; and
        an engagement surface located intermediate the first end and the second end,
        wherein the second end of the lever is actuable to urge the engagement surface against the proximal end of the femoral canal preparation instrument to secure the proximal end of the femoral canal preparation instrument within the bore, wherein the second end of the lever is located within the elongate neck; and
a femoral canal preparation instrument.

15. The kit of claim 14, wherein the proximal end of the femoral canal preparation instrument includes a circumferential lip or groove for engagement with the engagement surface of the locking mechanism of the trial neck.

16. A method of attaching a trial neck to a femoral canal preparation instrument, the trial neck comprising:
a body portion including a bore for receiving a proximal end of a femoral canal preparation instrument;
an elongate neck extending from the body portion;
a locking mechanism comprising a lever having:
    a first end integral with the body portion;
    a second end; and
    an engagement surface located intermediate the first end and the second end,
    wherein the second end of the lever is actuable to urge the engagement surface against the proximal end of the femoral canal preparation instrument to secure the proximal end of the femoral canal preparation instrument within the bore, and wherein the second end of the lever is located within the elongate neck,
the method comprising:
    inserting the proximal end of the femoral canal preparation instrument into the bore; and
    actuating the second end of the lever to urge the engagement surface against the proximal end of the femoral canal preparation instrument.

17. The method of claim 16, comprising engaging an actuation member of the locking mechanism with the second end of the lever to actuate the lever.

18. The method of claim 17, wherein a proximal end of the actuation member comprises a connection feature, and wherein the method further comprises connecting a tool to the actuation member to the connection feature for actuating the actuation member.

19. The method of claim 16, further comprising viewing the actuation member through a window in the elongate neck of the trial neck.

* * * * *